United States Patent [19]

Bradley et al.

[11] 4,191,196

[45] Mar. 4, 1980

[54] PROFILOMETRY METHOD AND APPARATUS

[75] Inventors: William E. Bradley; Gerald W. Timm; William M. Klatt, all of Minneapolis; Wayne H. Graves, Minnetonka, all of Minn.

[73] Assignee: American Medical Systems, Inc., Minneapolis, Minn.

[21] Appl. No.: 696,318

[22] Filed: Jun. 15, 1976

[51] Int. Cl.$^2$ ............................................. A61B 5/10
[52] U.S. Cl. .................................... 128/733; 128/748
[58] Field of Search ............ 128/2.1 R, 2.1 M, 2.1 E, 128/2 R, 2 S, 2 N, 2.05 D, 2.05 E, 349 R, 2 V, 642, 733, 748, 780

[56] References Cited

U.S. PATENT DOCUMENTS

| | | | |
|---|---|---|---|
| 3,628,538 | 12/1971 | Vincent et al. | 128/2.1 M X |
| 3,868,844 | 3/1975 | Klein | 128/2.05 D X |
| 3,974,826 | 8/1976 | Eggleton et al. | 128/2 V |
| 4,063,548 | 12/1977 | Klatt et al. | 128/2 R |
| 4,073,287 | 2/1978 | Bradley et al. | 128/2 R |

OTHER PUBLICATIONS

Ghoneim et al., "Urethral Pressure Profile", Urology, May 1975, vol. 5, No. 5, pp. 632–637.
Harvard Apparatus Co., Inc., "900 Series . . . Pumps", Bulletin 900, Jun. 1965, pp. 1–8.
Edwards et al., "The Urethral Pressure Profile . . . Application", Brit. J. of Urology, 1974, 46, 325–336.
Bradley et al., "Cystometric and Sphincter . . . Sclerosis", Neurology, Oct. 1973, vol. 23, No. 10, pp. 1131–1139.
Bradley et al., "Neuro-Urological Selection . . . Reflex", Neuro-Org. and its Relevance to Prosthetics, Intercontinental Med. Book Corp., New York, 1973, pp. 295–310.
Bradley et al., "Sphincter Electromyography", Urologic Clinics of North America, vol. 1, No,. 1, Feb. 1974., pp. 69–80.

Primary Examiner—Lee S. Cohen
Attorney, Agent, or Firm—Williamson, Bains, Moore & Hansen

[57] ABSTRACT

A method and apparatus for diagnostic evaluation of the urinary tract. The method comprises the steps of generating a urethral pressure profile and simultaneously monitoring and recording electrical signals derived from the urinary tract thereby generating an electrical or electromyographic profile. As fluid is inputted into the urethra the catheter is mechanically withdrawn therefrom at a constant velocity. Fluid pressure within the urethra is derived and recorded thereby providing a urethral pressure profile. Simultaneously, urethral electrical signals derived from one or more electrodes mounted on the catheter are amplified and graphically displayed, thereby plotting urethral electrical activity and urethral fluid pressure at given points along the urethra. The apparatus comprises an interface unit for withdrawing the catheter and for enabling measurement of the various diagnostic parameters.

5 Claims, 8 Drawing Figures

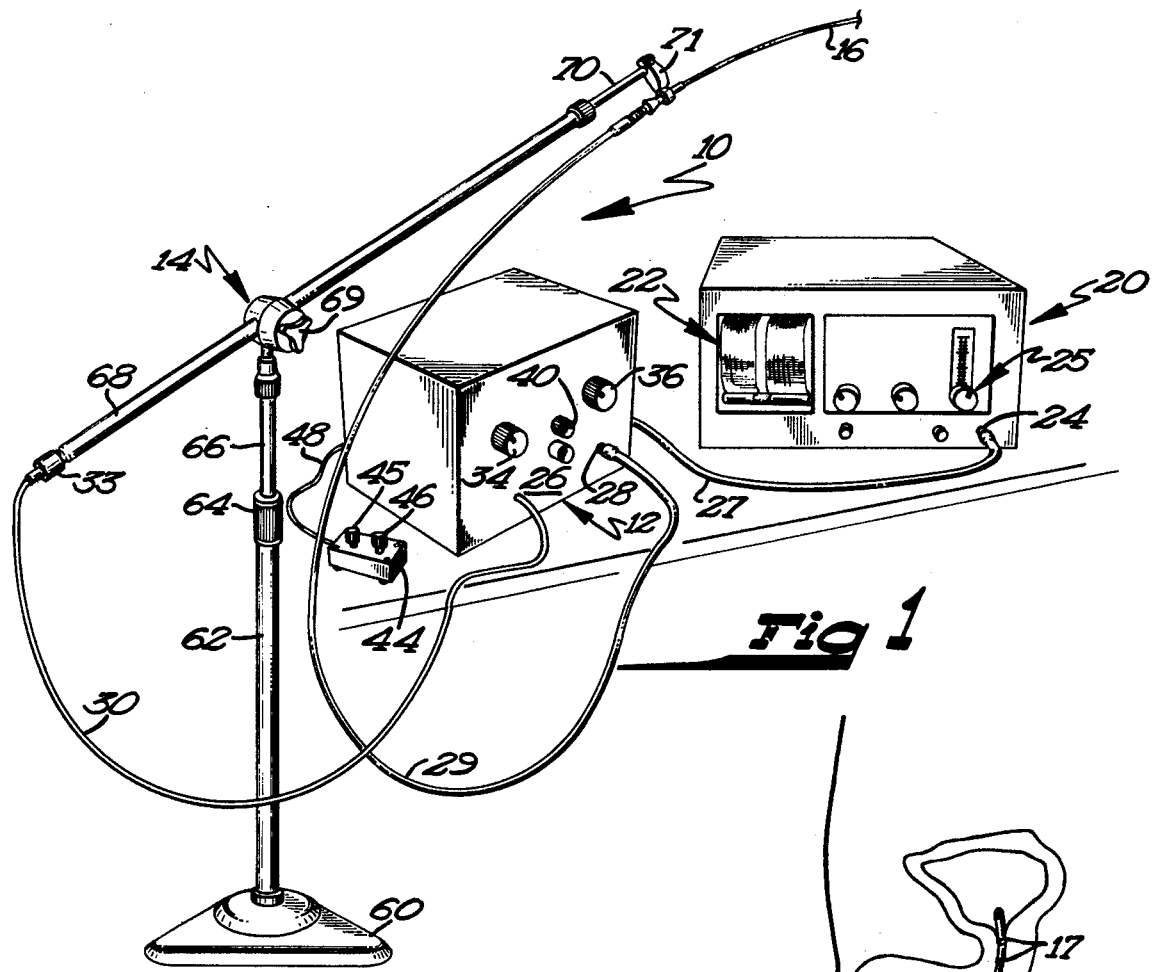

PROFILOMETRY METHOD AND APPARATUS

BACKGROUND OF THE INVENTION

This invention relates generally to the diagnostic evaluation of the urinary tract. More particularly, this invention relates to urethral profilometry, and an improved method for generating a urethral pressure profile.

Malfunction of the complex urinary tract can result in a variety of objectionable and unfortunate problems. One of the most common problems associated with urinary dysfunction is incontinence, or the inability to volitionally control micturition. One technique for investigating urinary dysfunction is cystometry. Cystometry measures vesical innervation and the elastic characteristics of the bladder wall. The cystometrogram which is generated by the latter process correlates internal bladder pressure with a volume of fluid injected therewithin. Another urinary investigative technique is electromyography, in which the electrical responses of the sphincters are monitored and displayed. The latter two techniques, as well as background material relevant to cystometry, electromyography and profilometry techniques, are discussed in a co-pending patent application entitled Method and Apparatus for Performing Micturition Analysis, filed on Apr. 7, 1975 bearing Serial No. 566,044, now U.S. Pat. No. 4,063,548, which is owned by the same assignee as in the instant case and is hereby incorporated by reference.

Profilometry, the urinary diagnostic technique most relevant to the instant invention, involves the generation of a urethral pressure profile. The urethral pressure profile is a graphical record of pressure within the urethra at successive points along its length. It is known that continence will be maintained if the intraurethral pressure is greater than the intravesical pressure. Leakage of urine occurs when urethral pressure decreases to less than bladder pressure. The utility of the urethral pressure profile as a diagnostic technique is thus indicated.

In the prior art urethral pressure profiles have been generated by retrograde installation of fluid into the urethra until the pressure was sufficient to overcome the sphincter resistance thereby forcing fluid into the bladder. Fluid filled pressure balloons have been utilized as a method of measuring urethral pressure, but such apparatus has a disadvantage of measuring pressure over a finite length of the urethra, equivalent to the length of the balloon rather than pressure at consecutive points. Another technique involves the insertion of a catheter internally of the urethra, and the subsequent measurement of urethra pressures along the length of the urethra as the catheter is withdrawn. By graphically displaying the results on a strip chart, for example, a correlation of urethral pressure versus position within the urethra will be provided. Usually the catheter is withdrawn mechanically, although manual withdrawal has been practiced. Various urethral pressure profile systems are discussed in the *British Journal of Urology*, Vol. 46, pages 325 to 336 (1974); *Urology*, Vol. 5, No. 5, May, 1975, page 632; and *Urological Research*, Vol. 1, pages 97-100 (1973).

Other pertinent U.S. patent references relevant to the instant invention are as follows:

U.S. Pat. No. 3,897,682, issued Aug. 5, 1975 to A. E. Brooks;
U.S. Pat. No. 3,628,538, issued Dec. 21, 1971 to Vincent et al.;
U.S. Pat. No. 3,641,993, issued Feb. 15, 1972 to Gaarder et al.;
U.S. Pat. No. 3,774,593, issued Nov. 27, 1973 to Hakata et al.;
U.S. Pat. No. 3,815,611, issued Nov. 26, 1971 to R. H. Denniston;
U.S. Pat. No. 3,674,010, issued July 4, 1972 to J. Falenks;
U.S. Pat. No. 3,437,088, issued Apr. 8, 1969 to L. J. Bielinski;
U.S. Pat. No. 3,870,072, issued Mar. 11, 1975 to H. Lindemann.

When a urethral pressure profile has been generated, those areas within the urethra which are unable to maintain the correct pressure will be identified by characteristic graphical inflections. Since successive points along the urethra will be identified along the horizontal axis of the graph, those portions of the urethra requiring further investigation will be diagnostically exposed. Thus the urethral pressure profile technique provides a valuable diagnostic aid.

It is also known that the urethra produces a variety of electrical signals which may be analyzed to provide useful diagnostic information. The functioning of sphincter muscles, for example, can be investigated through the process of electromyography as described in the above-mentioned co-pending patent application. It is thus advantageous to derive urethral electrical signals during generation of a urethral pressure profile.

SUMMARY OF THE INVENTION

The instant invention comprises a method and apparatus for performing diagnostic profilometry whereby a urethral pressure profile is generated and recorded simultaneously with the recording of electromyographic electrical signals derived from the urethra.

The method comprises the steps of catheterizing a patient and inputting fluid through a catheter into the urethra, withdrawing the catheter at a preferably constant velocity, and measuring and recording intraurethral pressure as the catheter is withdrawn. Since the catheter is withdrawn at a preferably linear rate, a strip chart recorder, for example, will indicate the approximate location internally of the urethra at which a particular pressure occurs.

Simultaneously as the catheter is withdrawn electrical signals are sensed by one or more electrodes mounted on the catheter and electrical activity within the urethra is then displayed simultaneously with the urethral pressure profile. By comparing the graphical results the attendant physician or urologist will be able to quantitatively diagnose urinary dysfunction. More particularly pressure variations within the urethra and the locations of same, along with corresponding simultaneously occurring electrical activities or responses, will be permanently indicated on a strip chart. Simultaneous measurement of electrical activity and pressure variations facilities differentiation between neurological and anatomical causes of urological dysfunction.

The diagnostic apparatus disclosed herein comprises an interface unit adapted to be interconnected between a catheter and a recording cystometer. The unit comprises pulling apparatus for slowly withdrawing the catheter from the patient and apparatus for supplying gas to the catheter. Since the unit is adapted to be interconnected with a recording cystometer, a urethral pressure profile will be generated as the catheter is withdrawn from the patient. Furthermore, the apparatus is provided with an interconnection to a recording electromyograph whereby electrical information derived from electrodes preferably mounted on the catheter will be recorded on the electromyograph thereby providing a simultaneously generated urethral electrical profile. Circuit means are included to control the speed at which the catheter is withdrawn from the patient.

Thus a primary object of this invention is to provide a diagnostic method and apparatus for investigating the urethra.

Another object of this invention is to provide a method for generating a urethral pressure profile.

It is the still further object of this invention to provide a method of the character described which will indicate urethral pressures as well as the location of same, and simultaneously indicate corresponding electrical activity within the urethra.

A still further object of this invention is to provide a method of the character which is adapted to derive electrical signal activity as a urethral pressure profile is generated.

Yet another object of this invention is to provide apparatus for enabling practice of the said method with existing urinary diagnostic apparatus.

These and other objects of this invention, along with features of novelty appurtenant thereto, will appear or become apparent in the course of the following description.

BRIEF DESCRIPTION OF THE DRAWINGS

In the following drawings, which form a part of the specification and are to be construed in conjunction therewith, and in which like reference numerals have been employed to indicate like parts in the various views:

FIG. 1 is a perspective view of apparatus constructed in accordance with the teachings of this invention;

FIG. 2 is a simplified diagram of a human urethra showing proper placement of the inserted catheter used with the instant invention;

FIG. 3 is a rear plan view of the urethral profilometry unit shown in FIG. 1;

DETAILED DESCRIPTION OF THE DRAWINGS

Figure 4:
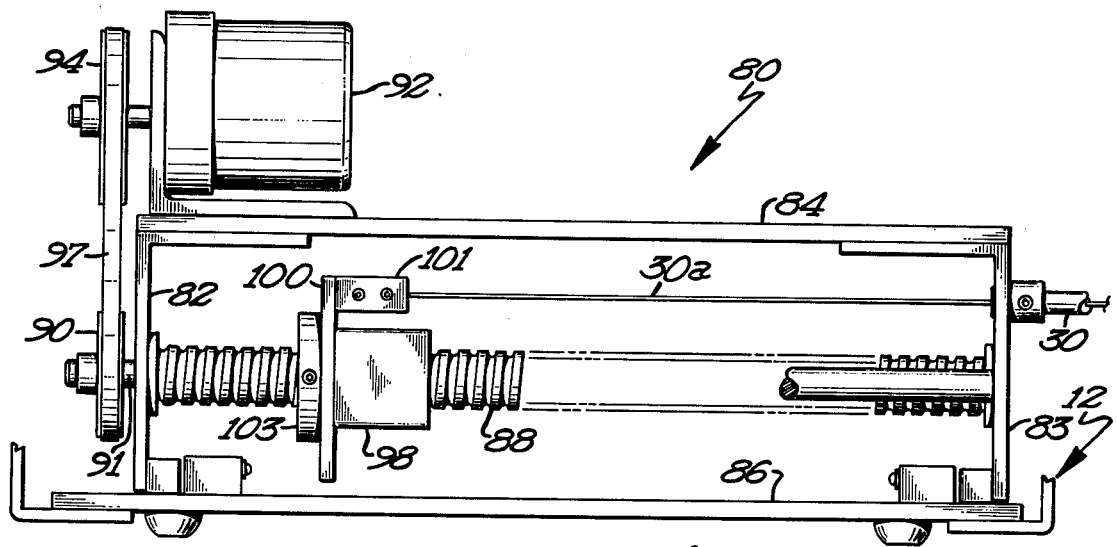
FIG. 4 is a side view of the lead screw apparatus enclosed within the urethral profilometry unit disclosed in FIG. 1.

Apparatus 10 (FIG. 1) comprises a generally cubical diagnostic interface unit 12 which is adapted to controllably activate an associated puller unit 14 in order to facilitate diagnostic profilometry. The interface unit 12 is mechanically linked to puller 14, which will slowly slidably withdraw catheter 16 (FIG. 2) from the urethra of a patient. Proper placement of a catheter 16 within a human urethra is illustrated generally in FIG. 2. One catheter suitable for use with the instant invention is disclosed in a co-pending application entitled "Urethral Profilometry Catheter and Method of Making Same," filed on Apr. 5, 1976, bearing Ser. No. 674,061, now U.S. Pat. No. 4,073,287, and owned by the same assignee as in the instant case. Catheter 16 preferably includes a pair of electrodes 17 for sensing electromyographic signals internally of the urethral tract 15, and a pair of conductors 19a and 19b for delivering sensed signals externally of the catheter. As the catheter 16 is withdrawn from the patient's urethral tract by the puller unit 14, sensed urethral electrical signals developed across electrodes 17 will be processed and graphically plotted. Simultaneously, a urethral pressure profile will be derived by measuring and plotting gas pressures within the urethra as the catheter is withdrawn.

Also depicted in FIG. 1 is a combined cystometer sphincter electromyography unit 20 which includes a strip chart recorder section 22 and a gas outlet nozzle 24 for supplying gas to the interface unit 12. The apparatus 20 includes electronic cystometry circuitry for activating the associated strip chart recorder section 22 in response to variations in gas pressure. Electromyographic circuitry is also provided to record urethral electrical signals served by the catheter. The gas cystometer-sphincter electromyograph 20 is disclosed in a co-pending patent application entitled "Method and Apparatus for Micturition Analysis," filed on Apr. 7, 1975, bearing Ser. No. 566,044, and owned by the same assignee as in the instant case. It is to be noted, however, that alternatively a conventional gas infusion unit including a source of gas, a pressure transducer, and an XY recorder, for example, may also be employed successfully in combination with the apparatus 10.

Figure 5:
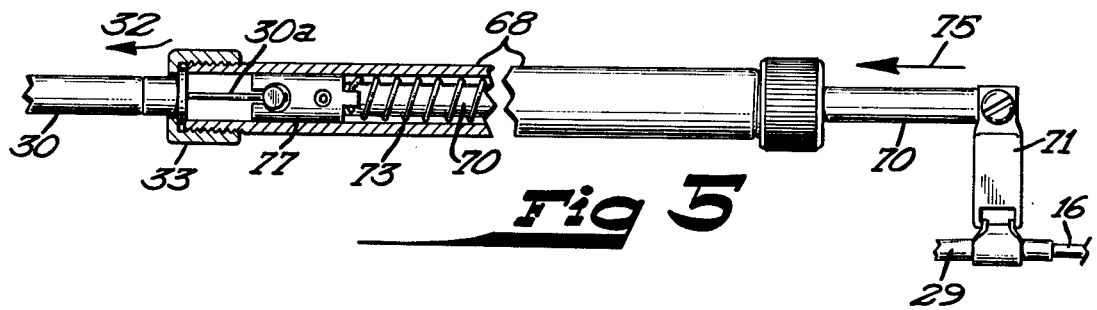
FIG. 5 is an enlarged fragmentary view of the puller unit shown in FIG. 1, with parts thereof broken away or shown in section for clarity.

The front panel 26 of unit 12 includes a gas outlet nozzle 28 for supplying gas to the catheter through an outlet tube 29. A puller cord 30 extends from the unit 12 and is attached at an end 32 (FIG. 5) of the puller unit 14. When the power control switch 34 is manually activated, apparatus to be later described within the unit 12 will exert a pulling force transmitted through cable 30 to the puller unit 14, thereby slowly removing the catheter 16 from the patient's urethra. The speed of withdrawal may be set by a speed control switch 36, which provides adjustments of withdrawal speed. In the preferred embodiment the apparatus is adapted to provide withdrawal speeds of between 0.5 and 50 centimeters per minute. Once the puller unit has moved to the fully retracted position as when the urethral profilometry test is completed, the puller may be returned to a fully extended position by activating a return button 40 on front panel 26.

A rear view of the urethral profilometry unit 12 is disclosed in FIG. 3. It will be noted that a rearwardly extending gas inlet nozzle 42 is provided for receiving a source of gas or fluid, such as provided by outlet nozzle 24 on the unit 20 (FIG. 1) or from a conventional cystometer. A conventional tubular hose 27 (FIG. 1) extends between inlet nozzle 42 and gas outlet nozzle 24. A remote control module 44 which includes controls 45 and 46 for respectively initiating the profilometry operation and for marking certain events on the strip chart apparatus 22, is adapted to be rearwardly connected to the apparatus 12 through a conductor cable 48 and a conventional electrical connector 50. An electrical input jack 52 is adapted to receive electrical signals picked up by the electrodes on the profilometry catheter, and an output jack 54 is provided to output electromyographic signals to suitable recording apparatus (such as the strip chart within the unit 20).

The puller unit 14 (FIGS. 1 and 5) comprises a conventional weighted puller base 60 on which a vertically upwardly extending stanchion 62 is threadably mounted. A height adjustment ring 64 facilitates variable, slidable adjustment of coaxially disposed vertical segment 66 with respect to stanchion 62. A generally transverse puller boom section 68 may be positioned by adjustment of a knob 69 which may be tightened to maintain the boom 68 in a convenient angular position with respect to the patient. A puller rod 70 which extends outwardly from casing 68 terminates in a catheter clamp 71 which is adapted to be attached to the catheter for the profilometry operation. The leftward end 32 of puller casing 68 is threaded to receive a fitting 33 enabling attachment of puller cable 30. The internal puller cable 30a is attached to an internal fitting 77 fastened to a slide rod 70 interiorly of the puller housing 68. Coil spring 73 acts to spring bias said slide rod 70 such that said internal fitting 77 is forced in the direction opposite to that of the arrow 75.

The lead screw assembly 80 (FIG. 4) is located interiorly of the interface unit 12 and controllably actuates the puller cord 30 to thereby remove the catheter from the urethra by activating the catheter puller 14. The lead screw device 80 includes front and rear brackets 82 and 83 which are disposed between upper and lower frame plates 84 and 86 respectively. A longitudinally extending threaded lead screw 88 is journalled for rotation within spaced apart plates 82 and 83. As the lead screw 88 rotates, a ball nut unit 98 will be moved leftwardly (as viewed in FIG. 4) thereby pulling the lead screw cable 30a. Cable 30a is attached to a follower plate 100 via an adapter attachment 101. Leadscrew nut 103 is mounted upon said ball nut 98 and acts to secure said follower plate 100 to said ball nut 98. In response to initiation of a command generated by a selection of speed control switch 36, synchronous motor 92 will be activated thereby causing the ball nut apparatus 98 to withdraw the catheter (via the linkage thereshown) from the patient's urethra. Motor 92 is linked to lead screw 88 via pulleys 90 and 94 and a belt 97. Pulley 90 drives an axle 91 which in turn rotates lead screw 88.

Figure 6:
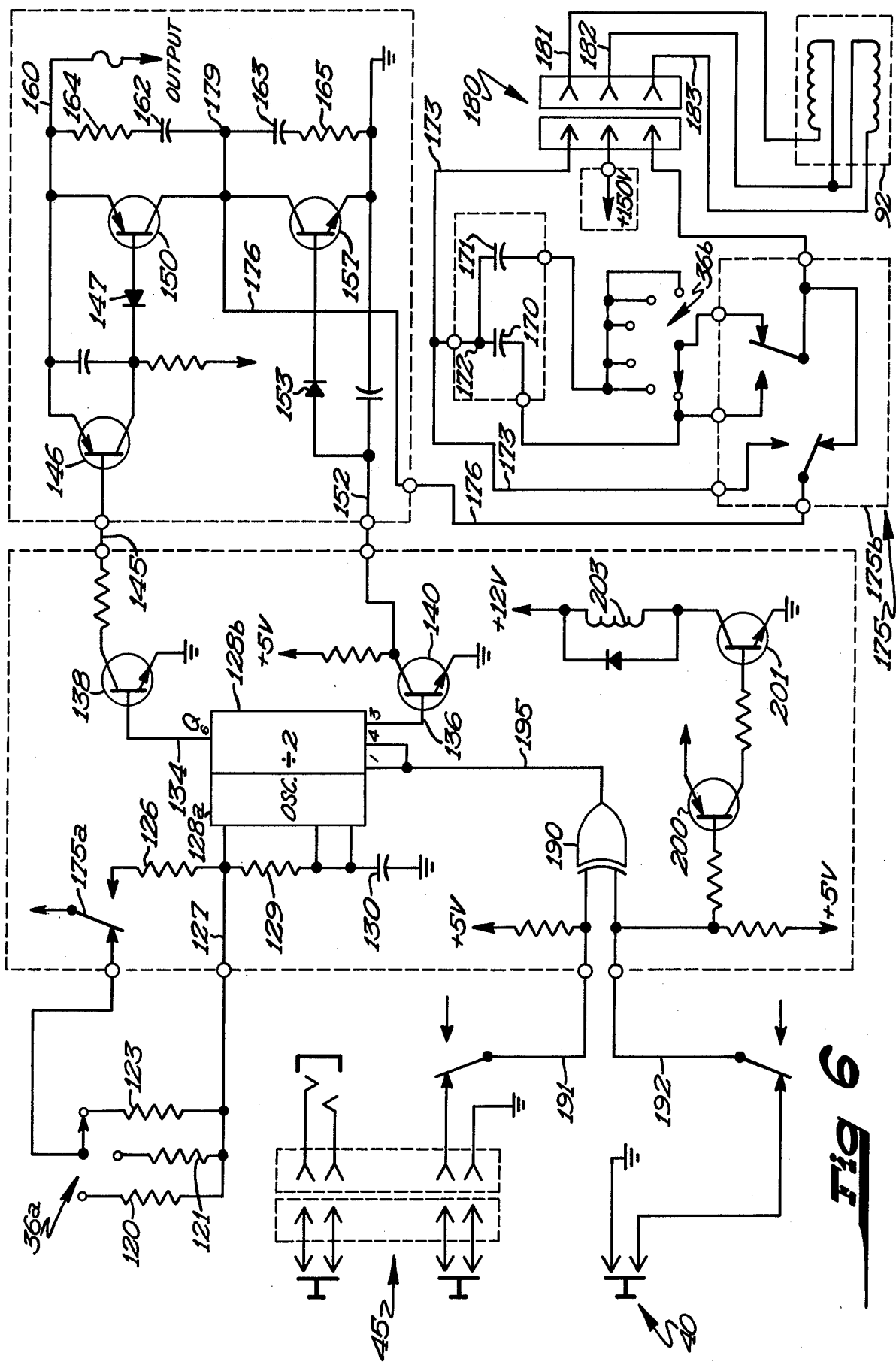
FIG. 6 is an electronic schematic diagram of the urethral profilometry unit shown in FIGS. 1 and 4.

Electronic circuitry included within the unit 12 is disclosed in FIG. 6. Speed control of motor 92 (and thus the rate of catheter withdrawal) may be determined by selection of one of three fixed resistors 120, 121 and 123 by a section 36a of rotary switch 36. Each of the resistors 120, 121 and 123 is connected to a conventional oscillator timer 128a through a line 127. The time constant determined by the combination of the resistor selected by switch 36a, resistors 126 and 129 and a capacitor 130 determines the duration of the fixed pulses outputted by oscillator 128a. Profilometry withdrawal speeds of between 0.5 centimeters per minute, and 25 centimeters per minute, for example, may be achieved by varying the time constant of the RC circuit. The output of divider 128b comprises complementary output pulses Q and $\bar{Q}$ appearing on output lines 134 and 136, respectively. The $\bar{Q}$ signal alternately turns transistor 138 off and on, and the Q signal alternately triggers transistor 140, so that transistors 138 and 140 are never on at the same time. The output of transistor 138 appears along line 145 and is coupled through a level shifting transistor 146 and a diode 147 to an amplifier transistor 150. The output of transistor 140 appears along line 152 and is transmitted through a diode 153 to a complementary amplifying transistor 157. The output developed between line 160 and ground, across transistors 150 and 157, is a 300 volt peak-to-peak symmetrical square wave which is sufficient to drive the synchronous motor 92 in the lead screw unit 80 (FIG. 4).

Capacitors 162 and 163 and resistors 164 and 165 are connected across the outputs of transistors 150 and 157 to provide protection from inductive transients generated by the motor. Section 36b of the rotary speed selector switch 36 selects an appropriate motor phase shift capacitor 170 and 171, ends of which are tied to a node 172 and connected through a line 173, a relay 175, and a return line 176 to a node 179 at the junction of capacitors 162 and 163. Current is delivered to motor 92 through a quick disconnect jack 180 and a trio of conductors 181 through 183.

Motor 92 may be reversed by activating relay 175 to thereby energize line 181 or 183. When the catheter is being withdrawn during profilometry, the pull switch 45 associated with event marker box 44 will be activated. An exclusive OR gate 190 receives a first input from pull switch 45 along a line 191. A second input is derived from return switch 40, which is located on the front panel of interface unit 12, along a line 192. If one, but not both, of the inputs to exclusive OR gate 190 is at ground potential, OR gate 190 will transmit an enable signal through line 195 to divider 128b. When neither input to OR gate 190 is grounded the enable signal on line 195 will go low, and as a result transistors 150 and 157 will be turned off, thereby stopping the motor 92.

When activated, puller return switch 40 grounds line 192, thereby providing an input to OR gate 190 and also activating transistors 200 and 201, to thus activate relay field winding 203. Relay field winding 203 operates relay 175 thereby reversing direction of the motor 92. Relay section 175b thus selects phase shift capacitor 170 and relay section 175a selects speed determining resistor 126 for maximum reverse speed. The reverse speed is of course independent of the setting on speed switch 36a. After the puller rod is extended out of the puller casing the maximum amount, it may be reattached to a catheter and another profilometry run may be initiated.

OPERATION

Figure 7:
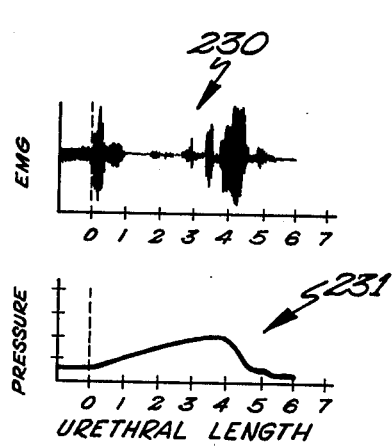
FIG. 7 shows an electrical urethral profile and a urethral pressure profile from a healthy female volunteer obtained through the practice of this invention.
Figure 8:
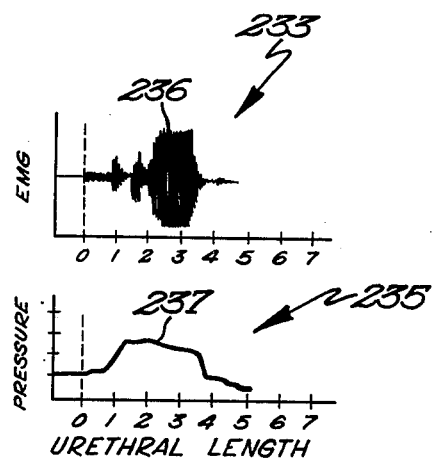
FIG. 8 is an electrical urethral profile and a urethral pressure profile obtained through the practice of this invention from a female patient affected with spasticity of the pelvic floor and periurethral striated musculature.

In operation a source of fluid (preferably gas) is connected to the interface unit 12 which is in turn connected through a gas line 29 to the catheter 16. A desired withdrawal speed is selected by adjustment of rotary switch 36. As the catheter is subsequently withdrawn from the patient's urethra by the then activated puller apparatus, electrical signals will be derived from the urethra and the pressure variations from insufflated gas will be derived and plotted by apparatus 20. In so doing graphical traces such as represented in FIGS. 7 and 8 may be derived. After the catheter is totally withdrawn from the patient, the puller unit may then be reset by activating button 45 on puller unit 44.

In FIG. 7 a first graph 230 indicates electromyographic signals derived along the length of the urethra as the catheter is withdrawn. A corresponding graph 231 indicates a urethral pressure profile, which is a plot of intraluminal pressure against urethral length. The diagnostic results shown in FIG. 7 were obtained from a healthy female volunteer in the supine position. It will be noted that maximum electromyographic electrical activity as well as maximum urethral intraluminal pressure occurs at approximately four centimeters along the urethral length axes.

Referring now to FIG. 8, there is seen graphs 233 and 235 which correspond to urethral electrical or electromyographic and urethral pressure profile traces obtained from a female patient affected with spasticity of the pelvic floor and periurethral striated musculature. Graph 235 indicates a relatively sharp rise in intraluminal pressure between approximately 1 and 2 centimeters, along the urethral length scale. Maximum electromyographic activity is indicated by waveform 236 appearing somewhat after the peak 237 in urethral pressure. During the tests shown, the recording paper output speed was 25 centimeters per minute, the gas infusion rate (selectable via control 25) was 150 cubic centimeters per minute, and the automatic electronic withdrawal rate was 12.5 centimeters per minute. It will thus be seen that integration of urethral pressure profile data with electromyographic or electrical urethral profile data provides a valuable diagnostic tool.

From the foregoing, it will be seen that this invention is one well adapted to obtain all the ends and objects herein set forth, together with other advantages which are obvious and which are inherent to the structure.

It will be understood that certain features and sub-combinations are of utility and may be employed without reference to other features and sub-combinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

What is claimed is:

1. A diagnostic profilometry method comprising the steps of:
   generating a urethral pressure profile, said generating step including the steps of:
      catheterizing a patient with a urethral catheter having a plurality of electrodes mounted thereon;
      inputting fluid through said catheter into the urethra;
      withdrawing said catheter from the urethra; and
      measuring and recording intra-urethral fluid pressure as said catheter is withdrawn; and
   generating a urethral electromyographic profile simultaneously with the generation of said urethral pressure profile as said catheter is withdrawn by monitoring urethral electrical activity with said plurality of electrodes mounted on said urethral catheter and recording said urethral electrical activity.

2. The method as defined in claim 1 wherein said monitoring step includes the employment of at least two electrodes mounted in spaced apart relationship on said catheter.

3. The method as defined in claim 1 wherein said withdrawing step comprises the steps of:
   attaching said catheter to a puller unit;
   activating said puller unit by energizing a motor to thereby mechanically withdraw said catheter; and
   controlling the speed of said motor and thus the speed of withdrawal of said catheter with a variable frequency voltage source electrically interconnected with said motor.

4. Interface apparatus for deriving and recording urethral parameter profiles, said apparatus comprising:
   catheter means having at least one electrode mounted thereon;
   puller means attached to said catheter means for controllably withdrawing said catheter means from a patient's urethra at a predetermined rate;
   fluid source means in fluid flow communication with said catheter means for inputting fluid therethrough into said urethra;
   means for interconnecting said catheter means with external fluid pressure recording and monitoring means whereby the fluid pressure within said urethra is measured and recorded as said catheter means is withdrawn from the urethra, thereby generating a urethral pressure profile; and
   electrical connection means for delivering electrical signals picked up within the urethra by said electrode mounted on said catheter means to an external device for monitoring and recording said electrical signals as said catheter means is withdrawn from the urethra, thereby generating an electromyographic urethral profile simultaneously with the generation of said urethral pressure profile.

5. The combination as defined in claim 4 wherein said apparatus comprises:
   synchronous electric motor means for activating said puller means to selectively withdraw said catheter means;
   voltage supply means for energizing said motor means; and
   means for varying the frequency of said voltage supply means to selectively vary the speed at which said catheter means is withdrawn from the urethra.

* * * * *